United States Patent [19]

Ishiguro et al.

[11] Patent Number: 5,521,089
[45] Date of Patent: May 28, 1996

[54] PROCESS FOR TREATING YEAST WITH B-1, 3-GLUCANASE TO PRODUCE MICROCAPSULES FOR ENCLOSING HYDROPHOBIC LIQUIDS

[75] Inventors: Mamoru Ishiguro, Ibaraki-ken; Yutaka Shimura, Tsuchiura; Naomu Ishiwaki, Takasaki, all of Japan

[73] Assignees: Mitsubishi Paper Mills Limited; Kirin Brewery Company, Limited, both of Tokyo, Japan

[21] Appl. No.: 178,604

[22] Filed: Jan. 7, 1994

Related U.S. Application Data

[63] Continuation of Ser. No. 709,170, Jun. 3, 1991, abandoned.

[30] Foreign Application Priority Data

Jun. 5, 1990 [JP] Japan ................. 2-146595
Sep. 7, 1990 [JP] Japan ................. 2-235636

[51] Int. Cl.$^6$ ................. C12N 1/16; C12N 11/04; C12N 1/06; A61K 9/14
[52] U.S. Cl. ................. 435/255.2; 424/489; 426/62; 426/656; 428/402.2; 435/174; 435/177; 435/182; 435/243; 435/255.4; 435/259
[58] Field of Search ................. 435/255.1, 255.2, 435/255.4, 182, 174, 177, 243, 259; 426/62, 656; 424/489, 490, 935; 428/402.2, 402.24

[56] References Cited

U.S. PATENT DOCUMENTS

| | | | |
|---|---|---|---|
| B 498,208 | 4/1976 | Shank | 426/62 |
| 3,716,452 | 2/1973 | Kitamura | 435/206 |
| 4,001,480 | 1/1977 | Shank | 435/182 |
| 4,032,663 | 6/1977 | Kobayashi | 426/51 |
| 4,559,307 | 12/1985 | Hopkins | 435/256 |
| 4,696,863 | 9/1987 | Matsushita et al. | 428/402.2 |
| 4,992,540 | 2/1991 | Jamas et al. | 435/255 |

FOREIGN PATENT DOCUMENTS

| | | |
|---|---|---|
| 0085805 | 8/1983 | European Pat. Off. . |
| 0242135 | 10/1987 | European Pat. Off. . |
| 58-107189 | 6/1983 | Japan . |
| 63-88033 | 4/1988 | Japan . |

OTHER PUBLICATIONS

Rodriguez, R. L. et al. In: Recombinant DNA Techniques: An Introduction; Publisher: The Benjamin/Cummings Publishing Co. Inc; pp. 96–97, 1983.

Primary Examiner—David M. Naff
Attorney, Agent, or Firm—Cushman Darby & Cushman

[57] ABSTRACT

Microorganism cells such as *Saccharomyces* or *Candida* yeast cells are treated with an alkaline aqueous solution with heating and stirring or with a cell wall dissolving enzyme such as glucanase or mannase to obtain cells that function as microcapsules by rapidly taking up a large amount of hydrophobic liquid. Treatment with an alkaline aqueous solution is preferably carried out at a pH of at least 8 for at least 1 hour at a temperature of 20°–100° C. A preferred embodiment of enzyme treatment is with β-1,3-glucanase for about 30 minutes to 5 hours at pH 4–9 at a temperature of 30°–60° C. The treatments dissolve cell walls of the yeast such that the walls still have sufficient strength for enclosing hydrophobic liquids.

1 Claim, No Drawings

PROCESS FOR TREATING YEAST WITH B-1, 3-GLUCANASE TO PRODUCE MICROCAPSULES FOR ENCLOSING HYDROPHOBIC LIQUIDS

This is a continuation of application Ser. No. 07/709,170 filed on Jun. 3, 1991, now abandoned.

BACKGROUND OF THE INVENTION

FIELD OF THE INVENTION

The present invention relates to a process for producing microcapsules having a microcapsule wall film which comprises a cell wall of yeast. More particularly, it relates to a process for producing microcapsules according to which physical strength or film characteristics of microcapsule wall film can be freely controlled depending on uses thereof.

RELATED ART

Microcapsules are fine particles of 1 µm — several hundreds µm in particle size and enclose a liquid, a solid or a gas therein which is uniformly covered with a thin film. At present, microcapsules containing colorless or colored dyes, medicines, agricultural chemicals, perfumes, feeding materials and food materials are industrially produced.

Microcapsules are produced by forming a thin film around a substance having some property and thus, the property is also confined therein and if desired, the confined substance can be released by rupturing the film.

The following are known as effective processes for production of microcapsules.

(1) The coacervation process which uses gelatin (U.S. Pat. Nos. 2,800,457 and 2,800,458).

(2) The in-situ process by which a film is formed from the external phase (aqueous phase) (Japanese Patent Kokoku Nos. 36-9168 and 47-23165 and Japanese Patent Kokai Nos. 48-57892, 51-9079, 54-49984, and 54-25277).

(3) The interfacial polymerization process which utilizes the film forming reaction between internal phase and external phase.

Furthermore, processes for production of microcapsules are utilizing microorganisms. For example, U.S. Pat. No. 4,001,480 discloses a process which comprises encapsulating in fungi containing 40–60% of lipid a substance soluble in the lipid.

Japanese Patent Kokai No. 58-107189 discloses microorganism microcapsules prepared by allowing grown microorganisms containing at least 10 wt % of lipid in the cells and harvested from a culture medium (such as fat-producing yeasts and brewers' yeasts) to contain a liquid selected from lipid extending organic substances (such as aliphatic alcohols, esters, aromatic hydrocarbons, and hydrogenated aromatic hydrocarbons), then adding thereto a liquid which becomes a core material soluble in the lipid extending organic substances and solubilizing it, and thereafter, encapsulating the liquid.

The above-mentioned encapsulation processes (1), (2) and (3) can provide microcapsules having a dense wall film excellent in protection of the core material and some of them have been industrially widely employed, but these processes still have various problems. That is, the coacervation process (1) is complicated in operations of adjustment of pH, temperature and time for reaction and besides, it requires a long time for the encapsulating step.

The in-situ process (2) and the interfacial polymerization process (3) have the defects that they are not suitable for encapsulation of unstable substances or readily heat deteriorating substances because highly reactive film-forming materials are reacted at relatively high temperatures in these processes.

The microencapsulation process utilizing microorganisms used natural substances, a part of a living organism as the film-forming material and is utterly different from conventional processes in mechanism of microencapsulation. However, considering the examples mentioned in the above patent specifications, the process has the defects that amount of the hydrophobic liquid which the initially added yeast cells (wall material) can enclose therein is relatively smaller than in the processes industrially employed at present and besides, a long time is needed for encapsulation in order to incept the hydrophobic liquid in a large amount.

Based on these proposals, the inventors made microcapsules utilizing microorganisms and produced pressure-sensitive copying papers using the microcapsules and made comparison of color formation by application of pressure by a typewriter. As a result, it has been found that probably because the physical strength of the portion utilized as the film is higher than that of the film in the microcapsules obtained by the coacervation process (1) and the in-situ process (2), only relatively low color density could be obtained although dyes were coated on the resulting sheet in the same amount as in the case of the copying papers made using the microcapsules obtained by the processes (1) and (2), and in particular, it was difficult to obtain a large number of copies.

SUMMARY OF THE INVENTION

The present invention provides a process for producing microcapsules utilizing microorganisms which makes it possible to rapidly take a large amount of a hydrophobic liquid in the cells and the resulting microcapsules can be efficiently ruptured when the enclosed substance is to be released, but have a film whose strength is sufficient for normal handling.

The inventors have conducted research in an attempt to solve the above-mentioned problems in encapsulation using microorganisms and found that the problems can be solved by the following process. That is, the present invention provides a process for producing highly practical microcapsules comprising yeast cells in which a hydrophobic liquid is enclosed, wherein the yeast cells are subjected to a treatment for controlling the strength of yeast cell wall. More particularly, the present invention relates to a process for producing the microcapsules, characterized in that the yeast cells are treated with an enzyme which dissolves the yeast cell wall or treated in an alkaline aqueous solution.

DETAILED DESCRIPTION OF PREFERRED EMBODIMENTS

The yeast cell wall of microcapsules which is used in the present invention is a physically and chemically relatively strong film comprising glucan, mannan, chitin or the like, and as a result of extensive research conducted by the inventors on method of controlling the strength of the cell wall without damaging the function to protect the core material which should be possessed by the microcapsules, it has been found that a large amount of the hydrophobic liquid can be rapidly contained in the yeast cells by treating the yeast cells in an alkaline aqueous solution for a given period with heating and stirring or treating the yeast cells with an enzyme which dissolves the cell wall and then mixing the thus treated cells with the hydrophobic liquid to be confined therein, followed by encapsulation and that physical strength as microcapsules and release of the liquid contained therein can be freely controlled by changing the treating conditions depending on usages of the capsules. Thus, the present invention has been accomplished. It depends on usages of microcapsules which treatment should be employed, but when the microcapsules are used for pressure-sensitive copying papers, the treatment with enzyme is preferred, taking into consideration the time required for the treatment and the coloration of yeast.

The process for producing microcapsules of the present invention fundamentally comprises the following steps:

(1) a step of preparing a dispersion of yeast cells, (2) a step of treating yeast cells with an alkaline aqueous solution or an enzyme, (3) a step of preparing a hydrophobic liquid and mixing the hydrophobic liquid with the dispersion of yeast cells, and (4) a step of encapsulation with heating and stirring.

The steps (2) and (4) can be simultaneously carried out.

If desired, steps of washing, dehydration, drying and the like of yeast cells can be incorporated into the above steps.

PH of the alkaline aqueous solution used for controlling the strength of yeast cell wall is usually at least 8, preferably 9.0–13.0, more preferably 10.0–12.0. If pH exceeds the above range, the protecting function of the microcapsules greatly decreases and this is not preferred.

Time for treating with the alkaline aqueous solution is 1 hour or more, preferably 3 hours or more.

Treating temperature is determined by routine experiments depending on pH of the system and ionic strength, but usually is 20°–100° C., preferably 30°–60° C.

The alkaline substances used in the present invention include, for example, inorganic alkaline compounds such as ammonium hydroxide, sodium hydroxide, calcium hydroxide, sodium silicate, and potassium hydroxide and organic nitrogen compounds such as monoethanoldiamine, ethylenediamine, and diethylenetriamine. The present invention is not limited to these compounds. Of course, buffer solutions may be used.

In the treatment with alkaline aqueous solution, various organic solvents, dispersants, preservatives and the like can be added depending on the treating amount.

The yeast cell wall dissolving enzymes used as another means for treatment for controlling the strength of cell wall may be any enzymes which can dissolve the yeast cell wall. That is, cell wall of yeast comprises glucan, mannan, composites of these polysaccharides and protein, chitin, or the like and there may be used any enzymes which can dissolve these components. The cell wall dissolving enzymes used in the present invention include, for example, glucanase, mannase, and chitinase. Among them, glucanase and mannase are preferred. Especially preferred are enzymes mainly composed of β-1,3-glucanase which are produced by microorganisms. These enzymes may be used singly or in combination of two or more. These enzymes are available as reagents or the following commercially available enzymes mainly composed of these enzymes may be utilized.

Enzyme produced by *Arthrobacter luteus* (Zymolyase 20T manufactured by Kirin Brewery Co., Ltd.), enzyme produced by Basidiomycetes (Kitalase produced by Kumiai Chemical Industry Co., Ltd.), enzyme produced by Achromobacter (YL-05 produced by Amano Pharmaceutical Co., Ltd.).

Furthermore, various cell wall dissolving enzymes mentioned in Funazu and Tsuru, "Lytic Enzymes", Kodansha (1977), pages 169–191, and other enzymes can also be used.

The dissolving treatment is carried out for partially dissolving yeast cell wall to make a thin film or soften it. The degree of dissolution of cell wall is such that desired physical strength and/or film characteristics (for example, slow release) can be obtained depending on use of microcapsules produced. That is, addition amount of enzyme and treating conditions are set so as to obtain the desired film strength and other film characteristics by acting the yeast cell wall dissolving enzyme on yeast by conventional method or the enzyme reaction is stopped at the time when the desired film strength is obtained.

Optimum conditions for many enzymes are usually pH 4–9 and temperature 30°–60° C. and addition amount of enzymes is suitably 0.1–100 mg per 1 g of substrate. Optimum reaction time is set depending on the above conditions, but the reaction time is usually about 10 minutes or more, preferably about 30 minutes – about 5 hours. Termination of the enzyme reaction can be carried out by separating the yeast cell from the enzyme by centrifugation, washing or the like, by deactivating the enzyme by heating, adjustment of pH or using a deactivator, and by other suitable methods, which do not cause damage and deterioration of yeast cell wall. Specific termination point of the enzyme reaction can be chosen at which microcapsules suitable for the objective use can be obtained. How much the yeast cell wall has been dissolved can be judged by measuring total amount of saccharide present in filtrate of yeast cell dispersion since the cell wall is decomposed and comes to dissolve into the filtrate by enzyme reaction. For example, in the case of microcapsules used for pressure-sensitive copying paper, they must not be ruptured by heat or humidity or by various printing and form operation. In order to exhibit sufficient strength of capsules in these normal handling, it is preferred to adjust the saccharide dissolution rate to about 0.5 – about 40%, especially about 1 – about 20%. If the saccharide dissolution rate is less than the above range, the effect of the present invention is not sufficiently developed and if it is more than the above range, strength of the film of the resulting capsules is low and when the capsules are used for pressure-sensitive copying paper, they are readily ruptured by external factors such as heat, humidity and solvents and the pressure-sensitive copying paper becomes poor in commercial value. In some case, it may occur that yeast cell is ruptured during encapsulation and satisfactory capsules cannot be obtained. Said saccharide dissolution rate is given by the following equation in which a total amount of saccharide in said filtrate is determined in terms of glucose by phenol-sulfuric acid method:

$$\text{Saccharide dissolution rate} = \frac{\text{Total amount of saccharide in filtrate (g)}}{\text{Dry weight of intially added yeast cells (g)}} \times 100\ (\%).$$

The time at which the treatment with yeast cell wall dissolving enzyme is carried out in the process for producing microcapsules according to the present invention has no special limitation and the treatment can be conducted before or after the encapsulation step or it may be conducted simultaneously with encapsulation of hydrophobic liquid.

The "yeast" used in the present invention is a general term for microorganisms which proliferate by budding or division. Examples thereof are *Saccharomyces cerevisias, Saccharomyces rouxii*, and *Saccharomyces carlsbergensis* which belong to genus *Saccharomyces* and *Candida utilis*, *Candida tropicalis*, *Candida lipolytica*, and *Candida flaveri* which belong to genus *Candida*.

The yeast cells have various forms depending on their kind and are preferably close as much as possible to sphere and diameter of cell is preferably 1–20 μm.

The yeast cells used in the present invention may be in living state or dried state and besides may be in dead state with no proliferating ability.

The yeast cells may be those which have been subjected to suitable treatments, if necessary. These yeast cells contain components such as enzyme, protein, amino acid component, saccharide component, and nucleic acid component which are soluble in water or polar solvents. In order to contain the hydrophobic liquid in a large amount, there may also be used yeast cell residue which remains after extracting these components in the cells by various methods.

These yeast cells or yeast cell residues may be dispersed in an aqueous solution using a suitable dispersant, if necessary.

As the hydrophobic liquids to be contained in the yeast cells, there may be used any of those which are substantially water-insoluble liquids or which can be converted to liquid by heating. As examples of the hydrophobic liquids, mention may be made of oily liquids extracted from animals or vegetables such as cottonseed oil, soybean oil, corn oil, olive oil, castor oil, fish oil, various fatty acids, and various steroids, and besides, when the capsules are used for pressure-sensitive copying paper, mention may be made of paraffin oil, chlorinated paraffin, chlorinated diphenyl, dibutyl phthalate, dioctyl phthalate, dibutyl maleate, o-dichlorobenzene, alkylated naphthalenes such as diisopropylnaphthalene, and 1-phenyl-1-xylylethane. Dyes, perfumes, pharmacologically active substances, food materials, feed materials or the like are dissolved or dispersed in the hydrophobic liquids depending on purpose and then the liquids are encapsulated. The resulting microcapsules are used for pressure-sensitive copying paper cosmetics, medicines, foods, feeds, agricultural chemicals, etc. depending on the substances enclosed therein. If these substances per se are hydrophobic liquids immiscible with water-soluble liquid, they can be encapsulated as they are without being dissolved or dispersed in the above hydrophobic liquids.

Encapsulation of the hydrophobic liquid is carried out by allowing the hydrophobic liquid and the yeast cell to contact with each other for a given period of time. Specifically, encapsulation is carried out, for example, by mixing the hydrophobic liquid with a yeast cell dispersion prepared by dispersing the yeast cells in water or others using a suitable dispersant and stirring the mixture. Temperature at the mixing and stirring is not critical, but is preferably 20°–100° C. Time for the mixing and stirring is usually 1 hour or longer, but can be suitably set depending on the amount of the enclosed hydrophobic liquid and the temperature. In order to contact the yeast cells and the hydrophobic liquid in a more uniform state, it is preferred that the hydrophobic liquid is emulsified with an aqueous solution containing an emulsifier such as anionic or nonionic emulsifier and then this is added to and mixed with the yeast cell dispersion. Furthermore, if necessary, the encapsulation can be carried out with addition of pH regulator, preservative, ultraviolet ray deterioration inhibitor, antioxidant, water-resisting agent, and the like.

The present invention will be explained in more detail by the following nonlimiting examples. The weight of yeast cell in examples and comparative examples is the weight in dry state.

EXAMPLE 1

[Step of dissolution of components in the cell]

10 g of ethanol was added to 100 g of a dispersion containing 10 g of commercially available baker's yeast (live yeast [*Saccharomyces cerevisiae*] produced by Kanegafuchi Chemical Industry Co., Ltd.). Then, the dispersion was shaken at 40° C. for 24 hours in a rotary shaking culture device to dissolve away from the cells the water-soluble component in the cells. The solution was separated from the yeast cell residue by centrifugation and water was evaporated from the whole solution in a drier at 105° C. to leave 6.0 g of nonvolatile component and it was confirmed that 40 wt % of the initially added yeast cells was dissolved away.

[Step of treatment with alkali]

This yeast cell dispersion was subjected to centrifugation to remove the filtrate and only the residue was redispersed in 100 g of a phosphoric acid-sodium hydroxide buffer adjusted to pH 10.0 and was heated and stirred at 50° C. for 3 hours.

[Step of encapsulation]

Then, 22 g of a high boiling point hydrophobic liquid (trademark: Highsol SAS N-296 manufactured by Nihon Petrochemical Co.) containing 1.1 g of 3-N-methylcyclohexylamino-6-methyl-7-anilinofluoran (trademark: PSD-150, black coloring dye manufactured by Nisso Chemical Co.) as a hydrophobic liquid was added to 20 g of 0.5 wt % aqueous solution of nonionic surface active agent (trademark: Tween 80 manufactured by Kao Atlas Co.) as an emulsifier under vigorous stirring to obtain an emulsion of the hydrophobic liquid which had an average particle size of 8 μm. This emulsion was added to the dispersion of yeast cell residue treated with the alkaline aqueous solution, followed by shaking for 3 hours under the conditions of temperature 50° C. and stirring speed 200 rpm in a rotary shaker. As a result, all of the hydrophobic liquid was contained in the yeast cells and encapsulation was completed. This microcapsule dispersion was bar-coated at about 5 g/m$^2$ on a woodfree paper of 40 g/m$^2$ in basis weight to obtain an upper sheet for pressure-sensitive copying paper which was superior in color formation.

EXAMPLE 2

10 g of the commercially available baker's yeast used in Example 1 was added to 100 g of 0.5% aqueous solution of Alon T-40 (40% sodium polyacrylate solution manufactured by Toagosei Chemical Industry Co., Ltd.) adjusted to pH 12.0 with sodium hydroxide, followed by heating and stirring at 40° C. for 6 hours. After completion of the treatment, the filtrate was removed by centrifugation and then, total amount of the residue was again made to 100 g with 0.5% aqueous solution of Alon T-40 and pH was adjusted to 7.0 with acetic acid to prepare a yeast cell dispersion. Thereafter, microcapsules were obtained in the same manner as in Example 1. The resulting microcapsules were coated on a woodfree paper of 40 g/m$^2$ to obtain an upper sheet for pressure-sensitive copying paper which was superior in color formation.

Comparative Example 1

Encapsulation was carried out in the same manner as in Example 1 except that the emulsion of the hydrophobic liquid was added to the dispersion of the yeast cell residue without subjecting the dispersion to the alkali treatment. About 6 hours was required for all of the hydrophobic liquid being contained in the microcapsules. An upper sheet for pressure-sensitive copying paper was produced using the resulting microcapsules in the same manner as in Example 1.

Comparative Example 2

Dispersion of yeast cell was prepared in the same manner as in Example 1 except that yeast cell residue after subjected to dissolution treatment was separated by centrifugation, and redispersed in 100 g of a phosphoric acid-sodium hydroxide buffer of pH 6.0 as a treating solution and the dispersion was heated and stirred at 50° C. for 3 hours.

Using this yeast cell dispersion, encapsulation was carried out for about 6 hours in the same manner as in Example 1. A large amount of emulsified particles which were not able to be contained in the yeast cells were present in the resulting yeast cell dispersion.

Using this dispersion as it was, an upper sheet for pressure-sensitive copying paper was produced in the same manner as in Example 1.

Color formation of the upper sheets for pressure-sensitive copying paper and strength of microcapsules obtained in the above examples and comparative examples were evaluated by the following methods and comparison was conducted.

Color formation: The upper sheet was brought into overlying relationship with a lower sheet (Mitsubishi NCR Paper Super Article N-40 manufactured by Mitsubishi Paper Mills Ltd.) so that the coating surfaces contacted with each other and the upper and lower sheets in this relationship were passed once between a pair of rolls applied with a pressure of 15 kg/cm to form color. Color density of the color formed portion after lapse of 1 hour was measured by a commercially available color differential meter (ND-101P manufactured by Nihon Denshoku Kogyo Co.). (The smaller value obtained means the higher color density.)

Strength of capsules: The upper sheet and the same lower sheet as used in the above color formation test were brought into overlying relationship so that the coating surfaces contacted with each other and these were left to stand at 105° C. for 12 hours with application of a light loading of 5 kg/cm$^2$ and thereafter, reflectance of the surface of the lower sheet was measured. (The larger value obtained means the higher strength of the microcapsule wall. That is, those which are inferior in strength of wall are ruptured during heat treatment and the dye enclosed therein is transferred to the opposite lower sheet and as a result, a low reflectance is obtained.). The value used for evaluation was calculated by the following formula.

$$\text{Strength of microcapsule} = \frac{\text{Reflectance of color formed portion}}{\text{reflectance of untreated portion}} \times 100\ (\%)$$

Results of the evaluation on the respective sheets according to the above methods are shown in Table 1.

TABLE 1

|  | Color formation (%) | Strength (%) | Overall evaluation |
| --- | --- | --- | --- |
| Example 1 | 58.0 | 97.2 | ○ |
| Example 2 | 56.5 | 94.3 | ○ |
| Comparative Example 1 | 76.3 | 98.0 | Δ |

TABLE 1-continued

|  | Color formation (%) | Strength (%) | Overall evaluation |
| --- | --- | --- | --- |
| Comparative Example 2 | 82.4 | 54.3 | x |

Definition of overall evaluation:
⊚: Very preferable level in characteristics
○: Preferable level in characteristics
Δ: Acceptable, but not satisfactory level in characteristics
x: Unpreferable level in characteristics

EXAMPLE 3

[Step of dissolution of cell wall]

Yeast cell residue obtained by treating yeast cells in the same manner as in Example 1 was dispersed in a phosphoric acid-sodium hydroxide buffer adjusted to pH 8.0 to make up 100 g. To this dispersion was added mg of a yeast cell wall dissolving enzyme (trademark: Zymolyase 20T produced by Kirin Brewery Co., Ltd. and mainly composed of β-1,3-glucan laminalipentaohydrolase), followed by heating and stirring at 40° C. for 2 hours to dissolve the yeast cell wall. After the dissolution treatment, centrifugation and washing with water were carried out twice to remove the enzyme solution to make totally 100 g and then, pH was adjusted to 10.0 (at which Zymolyase hardly acts on the yeast cell).

[Step of encapsulation]

Then, 22 g of a high boiling point hydrophobic liquid (trademark: Highsol SAS N-296 manufactured by Nihon Petrochemical Co.) containing 1.1 g of 3-N-methylcyclohexylamino-6-methyl-7-anilinofluoran (trademark: PSD-150, black coloring dye manufactured by Nisso Chemical Co.) as a hydrophobic liquid was added to 20 g of a 0.5 wt % aqueous solution of a nonionic surface active agent (trademark: Tween-80 manufactured by Kao Atlas Co.) as an emulsifier under vigorous stirring to obtain an emulsion of the hydrophobic liquid which had an average particle size of 5 μm.

This emulsion was added to a dispersion of yeast cell residue treated with a yeast cell wall dissolving enzyme, followed by shaking for 3 hours in a rotary shaker under the conditions of temperature 40° C. and stirring speed 200 rpm. As a result, all of the hydrophobic liquid was enclosed in the yeast cells and microencapsulation was completed. The resulting microcapsule dispersion, as it was, was bar-coated at about 5 g/m$^2$ on a woodfree paper of 40 g/m$^2$ in basis weight to obtain an upper sheet for pressure-sensitive copying paper which was excellent in color formation.

EXAMPLE 4

Without the step of dissolution of the components in the cells carried out in Example 1, dissolution of cell walls was carried out by adding 10 g of the commercially available baker's yeast used in Example 1 to 0.5% aqueous sodium polyacrylate solution (trademark: Alon T-40 manufactured by Toagosei Chemical Industry Co. Ltd.) adjusted to pH 7.0 to adjust the total amount to 100 g, then adding thereto 6 mg of a yeast cell wall dissolving enzyme (trademark: Kitalase, an enzyme for preparing protoplast manufactured by Kumiai Chemical Industry Co., Ltd.) mainly composed of β-1,3-glucanase), followed by heating and stirring at 40° C. for 2 hours. After completion of the dissolution, centrifugation and washing with water were conducted twice to exclude the enzyme solution and then, the residue was again added to a 0.5% aqueous Alon T-40 solution to make totally 100 g and pH was adjusted to 10.0. Thereafter, microcapsules were obtained through the encapsulation step in the same manner as in Example 3. The resulting microcapsules were coated on a woodfree paper of 40 g/m² to obtain an upper sheet for pressure-sensitive copying paper which was excellent in color formation.

EXAMPLE 5

The yeast cell residue obtained through the step of dissolution of the components in the cells in the same manner as in Example 1 was added to a phosphoric acid-sodium hydroxide buffer adjusted to pH 6.5 to make up totally 100 g and to this dispersion was added 8.0 mg of Zymolyase 20T, followed by heating and stirring at 40° C. for 3 hours to dissolve the yeast cell wall. After completion of the dissolution, centrifugation and washing with water were carried out twice to eliminate the enzyme solution to make totally 100 g. Then, pH was adjusted to 10.0 (at which Zymolyase hardly acted on the yeast cell). Thereafter, microcapsules were prepared through the same encapsulation step as in Example 3 and an upper sheet for pressure-sensitive copying paper was made in the same manner as in Example 3.

Comparative Example 3

Without the step of dissolution of yeast cell wall, an emulsion of the hydrophobic liquid was added to the dispersion of the yeast cell residue and encapsulation was carried out for 3 hours in the same manner as in Example 3. A large amount of emulsified particles which were not able to be contained in the yeast cells remained in the resulting dispersion of the yeast cells. Using this dispersion as it was, an upper sheet for pressure-sensitive copying paper was obtained in the same manner as in Example 3.

Color formation of the upper sheets and strength of the microcapsules obtained in the above examples and comparative example were evaluated by the same methods as above. The results are shown in Table 2.

TABLE 2

|  | Color formation (%) | Strength (%) | Saccharide dissolution rate (%) | Overall evaluation |
| --- | --- | --- | --- | --- |
| Example 3 | 56.2 | 95.8 | 3.8 | ⊙ |
| Example 4 | 50.2 | 88.0 | 10.5 | ⊙ |
| Example 5 | 39.8 | 75.2 | 35.3 | ○ |
| Comparative Example 3 | 73.4 | 54.3 | ≈0 | x |

TABLE 2-continued

|  | Color formation (%) | Strength (%) | Saccharide dissolution rate (%) | Overall evaluation |
| --- | --- | --- | --- | --- |

Definition of overall evaluation:
⊙: Very preferable level in characteristics
○: Preferable level in characteristics
Δ: Acceptable, but not satisfactory level in characteristics
x: Unpreferable level in characteristics According to the present invention, it has become possible to freely control the film strength of the microcapsules prepared using yeast cells. For example, when the microcapsules prepared by the present invention are applied to pressure-sensitive copying paper, it has become possible to obtain color formability and physical strength of film which are by no means inferior to those obtained by the coacervation process or the in-situ process. Furthermore, by treating the yeast cells which are wall materials of microcapsules with an alkaline aqueous solution or a yeast cell wall dissolving enzyme before encapsulation, it has become possible to contain the hydrophobic liquid in a larger amount and at a higher rate than when the treatment is not carried out.

In addition, it has also become possible to freely control the film characteristics of the microcapsules and to control release of the core material. Therefore, they can be more effectively applied than conventional ones in the above-mentioned various uses.

What is claimed is:

1. A process for producing microcapsules which comprises treating cells of a yeast selected from the group consisting of *Saccharomyces* and *Candida*, with β-1,3-glucanase for about 30 minutes to about 5 hours at a pH of 4–9 and a temperature of 30°–60° C. to dissolve cell walls of said yeast so that saccharide of said cell walls is dissolved, resulting in a saccharide dissolution rate given by the following formula, of about 1% to 20%:

saccharide dissolution rate = (Total amount of saccharide in filtrate (g) ÷ Dry weight of initially added yeast cells (g)) × 100, said cell walls being dissolved to the extent that the cell walls continue to have sufficient strength as capsules under normal handling conditions of enclosing a hydrophobic liquid in the treated yeast cells, and harvesting said yeast cells.

* * * * *